US010384850B2

(12) United States Patent
Devine et al.

(10) Patent No.: US 10,384,850 B2
(45) Date of Patent: *Aug. 20, 2019

(54) ARTICLES AND METHODS FOR IMPROVED PACKAGING AND STORAGE OF CONSUMER PRODUCTS HAVING AN AROMA

(71) Applicants: Nicole Marie Devine, San Marcos, CA (US); Melissa Scorsone, San Marcos, CA (US)

(72) Inventors: Nicole Marie Devine, San Marcos, CA (US); Melissa Scorsone, San Marcos, CA (US)

(73) Assignee: Panache Pantry, Escondido, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/791,340

(22) Filed: Oct. 23, 2017

(65) Prior Publication Data
US 2018/0229908 A1 Aug. 16, 2018

Related U.S. Application Data

(63) Continuation-in-part of application No. 15/701,399, filed on Sep. 11, 2017, which is a continuation-in-part (Continued)

(51) Int. Cl.
*B65D 77/22* (2006.01)
*B65D 75/00* (2006.01)
(Continued)

(52) U.S. Cl.
CPC .......... *B65D 77/225* (2013.01); *A23L 3/3418* (2013.01); *A23L 3/3427* (2013.01);
(Continued)

(58) Field of Classification Search
CPC ..... B65F 77/225; B65B 31/00; B65D 77/225; A23L 3/00; A23L 3/001; A23L 3/34095; A23L 27/00
(Continued)

(56) References Cited

U.S. PATENT DOCUMENTS

284,536 A 9/1883 Brown
2,429,984 A 11/1947 Berglund
(Continued)

*Primary Examiner* — Viren A Thakur
*Assistant Examiner* — Chaim A Smith
(74) *Attorney, Agent, or Firm* — Acuity Law Group, P.C.; Daniels M. Chambers (57) ABSTRACT

Provided herein is a degassing valve for a dry consumer product (e.g., a dry foodstuff, a cannabis-containing medicinal or recreational product, etc.) that has an enticing or pleasant aroma. Such a valve includes a valve body, a one-way valve element positioned on the valve body, and, preferably, a filter associated with said valve body wherein the filter is configured to facilitate the passage of a gas. The gas may be selected from the group consisting of air, carbon dioxide, oxygen, nitrogen, and methane, or mixtures thereof. Additionally, the gas contains one or more aroma-conferring volatile molecule species responsible for the aroma characteristic of the product. The filter of the valve body may include activated charcoal, an activated charcoal mixture or a combination thereof. In some embodiments, the dry consumer product is a dry foodstuff such as flavored or seasoned breadcrumbs, spices, marijuana-containing products, or other flavorful dry consumer product, the aroma(s) of which can provide an important marketing benefit.

11 Claims, 1 Drawing Sheet

Related U.S. Application Data of application No. 14/714,116, filed on May 15, 2015, now Pat. No. 9,758,287.

(60) Provisional application No. 61/993,616, filed on May 15, 2014.

(51) Int. Cl.

| | | |
|---|---|---|
| *B65D 75/58* | (2006.01) | |
| *A23L 3/3427* | (2006.01) | |
| *A61L 9/12* | (2006.01) | |
| *B01D 53/02* | (2006.01) | |
| *A23L 3/3418* | (2006.01) | |

(52) U.S. Cl.
CPC ............... *A61L 9/12* (2013.01); *B01D 53/02* (2013.01); *B65D 75/008* (2013.01); *B65D 75/5805* (2013.01); *A23V 2002/00* (2013.01); *A61L 2209/14* (2013.01); *B01D 2253/102* (2013.01); *B65D 2575/586* (2013.01)

(58) Field of Classification Search
USPC .......................................................... 383/45
See application file for complete search history.

(56) References Cited

U.S. PATENT DOCUMENTS

| | | | |
|---|---|---|---|
| 3,595,467 | A | 7/1971 | Goglio |
| 3,799,427 | A | 3/1974 | Goglio |
| 4,000,846 | A | 1/1977 | Gilbert |
| 4,122,993 | A | 10/1978 | Glas |
| 4,134,535 | A | 1/1979 | Barthels et al. |
| 4,284,104 | A | 8/1981 | Beghini |
| 4,420,015 | A | 12/1983 | Blaser |
| 4,576,285 | A | 3/1986 | Goglio |
| 4,653,661 | A | 3/1987 | Buchner et al. |
| 4,705,174 | A | 11/1987 | Goglio |
| 4,890,637 | A | 1/1990 | Lamparter |
| 4,913,561 | A | 4/1990 | Beer |
| 4,953,708 | A | 9/1990 | Beer |
| 4,966,780 | A | 10/1990 | Hargraves et al. |
| 5,059,036 | A | 10/1991 | Richison et al. |
| 5,354,133 | A | 10/1994 | Rapparini |
| 5,419,638 | A | 5/1995 | Jamison |
| 5,515,994 | A | 5/1996 | Goglio |
| 5,532,011 | A | 7/1996 | Goglio |
| 5,688,544 | A | 11/1997 | Bolton et al. |
| 5,727,881 | A | 3/1998 | Domke |
| 5,782,266 | A | 7/1998 | Domke |
| 5,893,461 | A | 4/1999 | Walters |
| 5,992,635 | A | 11/1999 | Walters |
| 6,056,439 | A | 5/2000 | Graham |
| 6,070,728 | A | 6/2000 | Overby et al. |
| 6,468,332 | B2 | 10/2002 | Goglio et al. |
| 6,520,323 | B1 | 2/2003 | Colombo |
| 6,827,105 | B1 | 12/2004 | Marble et al. |
| 6,877,601 | B1 | 4/2005 | Colombo |
| 7,178,555 | B2 | 2/2007 | Engel et al. |
| 7,490,623 | B2 | 2/2009 | Rypstra |
| 7,637,283 | B2 | 12/2009 | Hoffman |
| 7,810,677 | B2 | 10/2010 | Py et al. |
| 7,874,731 | B2 | 1/2011 | Turvey et al. |
| 7,922,026 | B2 | 4/2011 | Westphal |
| 8,038,023 | B2 | 10/2011 | Moore et al. |
| 8,104,644 | B2 | 1/2012 | Py et al. |
| 8,342,203 | B2 | 1/2013 | Weaver et al. |
| 2003/0106589 | A1 | 6/2003 | Basso |
| 2006/0030472 | A1 | 2/2006 | Hartman et al. |
| 2012/0281933 | A1* | 11/2012 | Beer ..................... B65D 33/01 383/45 |
| 2014/0029873 | A1* | 1/2014 | Cruz ........................ B65B 9/20 383/45 |
| 2015/0166257 | A1 | 6/2015 | Trombetta |

* cited by examiner

ARTICLES AND METHODS FOR IMPROVED PACKAGING AND STORAGE OF CONSUMER PRODUCTS HAVING AN AROMA

CROSS-REFERENCE TO RELATED APPLICATIONS

This application claims the benefit of and priority to U.S. provisional patent application No. 61/993,616, filed on 15 May 2014, U.S. non-provisional patent application Ser. No. 14/714,116, filed on 15 May 2015, issued as U.S. Pat. No. 9,758,287, and U.S. non-provisional patent application Ser. No. 15/701,399, filed on 11 Sep. 2017, of which this application is a continuation-in-part. The contents of each of the foregoing applications (and patent(s)) is hereby incorporated by reference in its entirety for any and all purposes.

FIELD OF THE INVENTION

The present invention is related to improved packaging and storage of consumer goods or products having an aroma, preferably a pleasant or other aroma that promotes acquisition and/or use of the products, such as dry foodstuffs (e.g., spices, flavored breadcrumbs, ground coffee, cannabis, etc.), including those that do not require added preservatives to extend useful shelf life.

BACKGROUND OF THE INVENTION

The following description of the background of the invention is provided to aid in understanding the invention, but is not admitted to describe or constitute prior art to the invention.

It is well known that long term storage of consumer goods and products having appealing aromas, odors, etc. (e.g., dry foodstuffs) derived from or otherwise containing organic matter is hampered by the potential contaminating growth of microorganisms, loss of flavor, and/or decomposition resulting from oxidation over time, and the potential for the development of toxins, generally, over the useful shelf life of the product. Most manufacturers of such consumer goods compensate for this "spoilage" by adding chemical preservatives to the product. However, it is well known in the art that chemical preservatives sacrifice the quality, taste, and overall integrity of many goods, including foodstuff products. Those products that do not contain chemical preservatives, however, have a short shelf-life and are thus limited with regard to long-term use.

One largely successful approach to solving this problem has been the use of airtight, flexible, rigid, or semi-rigid packaging containers or vessels that contain a one-way degassing valve to allow the unidirectional outward flow of gases, including but not limited to oxygen, nitrogen, methane, and carbon dioxide, from the container. Most one-way degassing valves, such as those described in U.S. Pat. No. 5,515,994, were originally designed to preferentially exclude long chain organic molecules, those considered "aromatic" gases (i.e., gases that contain volatile compounds responsible for providing aromas that can appeal to consumers (including prospective consumers (i.e., shoppers)), from exiting the container by way of the degassing valve.

While efficient at preservation, that approach is limited with respect to effective consumer marketing because consumers (including prospective buyers or consumers (i.e., shoppers)) are not able to sample the product by way of smelling the product's ingredient(s) or aroma(s) prior to making a purchasing decision. Thus, there is a bona fide need for packaging containers and non-chemical preservation methods that can preferentially prevent outgassing from a container of long chain product-derived aromatic gases on one hand but be induced to exhale aromatic gases upon physical stimulation or the application of pressure (e.g., by a customer's squeezing of the container), such that aroma(s) emanating from the product packaged in the container may be sampled on demand by a consumer without compromising the integrity of the vessel, immediately reducing the risk of purchase (or if previously purchased, subsequent use) for the consumer. Such compositions and methods would be highly useful, but not limited to, the packaging and strategic marketing of consumer goods or products that have enticing and/or pleasant aromas, such as breadcrumbs and breadcrumb-based products, spices, and other dry, packaged food products the aroma(s) of which are an appealing and salient feature that may be exploited for enhanced marketing purposes.

SUMMARY OF THE INVENTION

The present invention is drawn towards packaging containers that can preferentially prevent the unwanted release from such containers of desirable pleasant aroma-providing chemical compounds on one hand and, on the other, be induced to exhale, exhaust, or otherwise release gas or vapor containing such compounds through a one-way degassing valve outlet upon physical stimulation or the application of pressure (e.g., by squeezing such a container) such that such compound(s) in the released gas (or vapor) may be sampled by way of smell and/or taste. Methods of making and using such containers are also included. The invention does nothing in the way of compromising the integrity of the packaging container or vessel and its ability to serve as a non-chemical preservation method. Such containers and methods have patentable utility in the packaging and strategic marketing of fragrant dry consumer goods or products such as dry food products (e.g., breadcrumbs and breadcrumb-based products, spices, etc.), recreational and/or medicinal products that contain cannabis or marijuana (or extracts or derivatives thereof), potpourri (i.e., mixtures of dried plant products, for example, dried flower petals and/or spices), household cleaning products (e.g., soaps and other dry or powdered cleaning products), etc., the aroma(s) from which is(are) an appealing and salient feature heretofore unexploited for enhanced marketing purposes. The utility of the present invention allows for the sampling of such aroma(s) while providing all of the preservative qualities of consumer product packaging that includes a unidirectional degassing valve.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

DETAILED DESCRIPTION OF THE INVENTION

As used herein, the term "aromatic gas" refers to a gas or vapor that contains a molecule or chemical compound having organic origin(s) (e.g., from a dry foodstuff or other dry consumer product an aroma from which, if sampled, could add marketing appeal to a prospective buyer) that can be detected by smell (or by smell and taste). As is known, a chemical compound has a smell or odor when it is sufficiently volatile to be transported to the olfactory system in the upper part of the human nose. Aromatic gases are known to contain aroma compounds, aromas, flavors, and flavorants (be they naturally occurring or synthetic). As is known, aroma compounds often form during the maturation or ripening of fruits and other crops, although compounds having an enticing and/or pleasant aroma may be derived from any suitable source, including isolation from plants, de novo synthesis, derivation from a naturally occurring compound, etc. They are also used in the production of flavorants, which are used, for example, in the food industry to flavor, improve, and generally increase the appeal of food products.

As used herein, the term "contamination" refers to the growth of microorganisms, including, but not limited to, fungi and bacteria.

As used herein, the term "long molecular chain" or "longer molecular chain" refers to long chain organic molecules, aromatics, or "aromatic" gases.

As used herein, the term "oxidation" refers to the exposure of the aroma conferring compound(s) in a consumer product (e.g., foodstuff) to an amount of atmospheric oxygen (or other oxidizing agents(s)) sufficient to significantly oxidize it.

Provided herein are packaging containers for storing dry consumer products, for example, dry food products, that allow a consumer to squeeze or otherwise manipulate the container so as to allow a sample of air or gas from inside the container to exit through a unidirectional degassing valve such that the volatile compound(s) responsible for the aroma(s) in the air in the container can pass through the valve and be sensed by the consumer, for example, prior to the consumer purchasing the product or, after purchase, prior to opening the container to dispense some or all of the product stored in the container.

Some embodiments of the invention include conventional unidirectional valve structures that have been adapted for use in conjunction with the invention, while in other embodiments, new unidirectional valves are utilized. For instance, such new valves do not include a filter designed to retain aromatic molecules inside a container of the invention while still allowing for gas to be forcibly expelled from the container. In some embodiments, the valve may be a degassing valve. Such valves include a valve body, a one-way valve element positioned on or with or in conjunction with the valve body, and a filter or frit.

In the context of the new valves of the invention, the filter is preferably configured to retain particulate matter, such as food particles, powders, etc., while permitting the passage of gas or air from the container, including the passage of aromatic compounds suspended in the gas that are being forcibly expelled from the container (e.g., by way of a consumer squeezing the container to sample gas from inside the bag, as may be done to sample the aroma of the product, assess the product's freshness or other aroma-related properties, etc.). The gas may be oxygen, nitrogen, carbon dioxide, methane, air, or an engineered mixture of gases designed to provide enhanced preservative characteristics for the particular type of consumer product (e.g., dry food products (e.g., breadcrumbs and breadcrumb-based products, spices, etc.), recreational and/or medicinal products that contain cannabis or marijuana (or extracts or derivatives thereof), potpourri (i.e., mixtures of dried plant products, for example, dried flower petals and/or spices), household cleaning products (e.g., soaps and other dry or powdered cleaning products)), etc. In other embodiments, the filter includes an element designed to retain gaseous aromatic compounds inside the container. For example, the filter can comprise activated charcoal. Additionally, the activated charcoal may be mixed with another suitable filtering compound or composition, including an activated charcoal mixture or any other suitable filtering compound known in the art.

In some embodiments, the aromatic gas may be an aroma. The aroma(s) present in particular package may be generated or associated with or evolved from the consumer product (e.g., dry foodstuff). It may occur naturally in one or more of the product's ingredients, or be added during the preparation of the product. An aroma may be a long molecular chain gas, for example, but may any be any suitable aroma compound. Particularly preferred are volatile organic molecules in a gas that a human can detect by smell and that yield an appealing or pleasant olfactory sensation when sampled.

During manufacture of packaged dry consumer products (e.g., dry foodstuffs, medicinal or recreational marijuana products) in accordance with the invention, the packaging container is allowed to retain air or gas, preferably decontaminated air or gas (e.g., air that has been HEPA filtered) such that the container is at least partially inflated. In contrast, packaging for many food products, e.g., coffee (ground or whole bean), that include a unidirectional degassing valve is typically evacuated or vacuum-sealed after being filled with the product to be packaged, and the degassing valve allows gases that evolve from the packaged consumer product (e.g., coffee beans, marijuana leaves, etc.) over time during storage in the package to escape from package once the cracking pressure of the valve element is exceeded, thereby preventing over-pressurization and, in some cases, failure of the packaging material, Packaging such as described in U.S. Pat. No. 5,515,994, incorporated by reference in its entirety, may in fact be used for this purpose. Unlike the valve structure described in U.S. Pat. No. 5,515,994, the valving structure of the invention may pass aromatic long chain gases. The present invention is based on the principle that if packaged appropriately, aromatic gases may indeed be physically induced to exit the bag containing the "unidirectional" degassing valve of U.S. Pat. No. 5,515,994, despite the presence of an intact charcoal (or other organic) filter.

In some embodiments, the valving structure may include one or more of the unidirectional degassing valves described in U.S. Pat. No. 7,284,536, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aroma-conferring gases from said container and into local atmosphere.

In some embodiments, the valving structure may include one or more of the unidirectional degassing valves described in U.S. Pat. No. 2,429,984, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 3,595,467, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 3,799,427, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,000,846, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,122,993, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,134,535, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,420,015, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,576,285, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,653,661, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,705,174, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,890,637, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include comprising one or more of the unidirectional degassing valves described in U.S. Pat. No. 4,913,561, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,953,708, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 4,966,780, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 5,059,036, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 5,354,133, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 5,419,638, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 5,532,011, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 5,727,881, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 5,782,266, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 5,893,461, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 5,992,635, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 6,056,439, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 6,070,728, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 6,468,332, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 6,520,323, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 6,827,105, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 6,877,601, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 7,178,555, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 7,490,623, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 7,637,283, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 7,810,677, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 7,874,731, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 7,922,026, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 8,038,023, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 8,104,644, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

In some embodiments, the valving structure may include one or more of the unidirectional degassing valves described in U.S. Pat. No. 8,342,203, incorporated by reference in its entirety, to package aromatic dry consumer products (e.g., dry foodstuffs, including but not limited to aromatic breadcrumb products, products containing dried cannabis, etc.). Such products are packaged into said container such that there is enough air present in said container to be used as a propellant, by way of squeezing or other forceful physical stimulus, to force aromatic gases from said container and into local atmosphere.

Provided herein is a packaging system for dry consumer products (e.g., dry foodstuffs such as flavored breadcrumbs and breadcrumb-based products, products, products containing dried cannabis, etc.) that have an appealing aroma that can be used for marketing and/or other purposes. As will be appreciated, dry consumer products (e.g., dry food products (e.g., breadcrumbs and breadcrumb-based products, spices, etc.), recreational and/or medicinal products that contain cannabis or marijuana (or extracts or derivatives thereof), potpourri (i.e., mixtures of dried plant products, for example, dried flower petals and/or spices), household cleaning products (e.g., soaps and other dry or powdered cleaning products)), etc., are generated by those skilled in the art. These products (e.g., foodstuffs, medicinal or recreational cannabis-containing products) are then further packaged for sale. Once the aroma-emitting product (e.g., flavored breadcrumbs, medicinal marijuana) is produced, it may be packaged by hand or automatically to achieve an optimal volume (or other amount) of product per package. In some embodiments, the range of possible volumes of the packaged dry consumer product (e.g., foodstuff) to the overall interior volume of the container may be between about 1% to about 99%, preferably from about 20-80%. In some embodiments, the optimal range of product volume to interior volume of the packaging container may be between about 70% to about 90%. Particularly preferred amounts of filled interior volume attributable to the packaged consumer product includes about any of 85%, 80%, 75%, 70%, 65%, 60%, 55%, 50%, 45%, 40%, 35%, 30%, 25%, 20%, 15%, and 10%.

Figure 1:
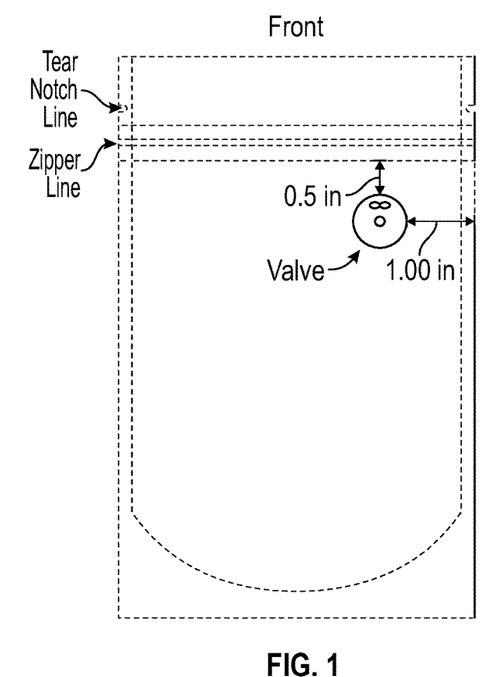
FIG. 1 shows one embodiment of a consumer product (here, a dry food stuff) package according to the invention that includes a unidirectional degassing valve that is visible and accessible to a consumer (or prospective consumer) so as to allow a consumer to sample gas (or vapor) from inside the container prior to purchase so that consumer can sense the aroma(s) associated with the dry food products packaged in the container.
Figure 2:
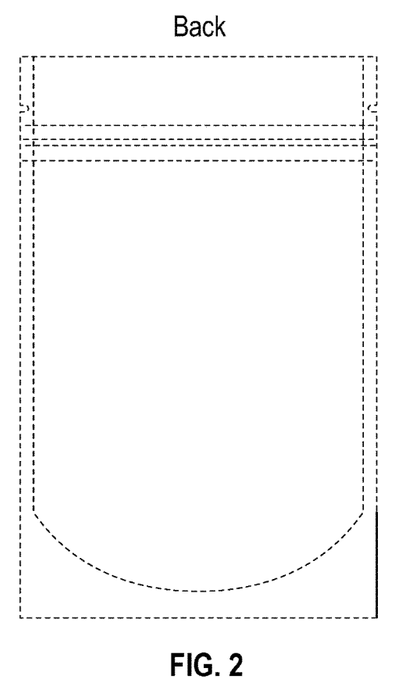
FIG. 2 shows a back view of the container shown in FIG. 1.
Figure 3:
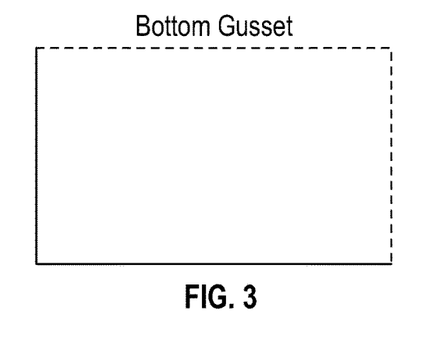
FIG. 3 shows a view of the bottom gusset used to produce a container as shown in FIGS. 1 and 2.

A particularly preferred dry consumer product useful in the context of the invention is flavored or seasoned breadcrumbs. Breadcrumbs (such as plain or seasoned or flavored bread crumbs) may be dispensed into a package, such as the non-limiting example of a four-ounce stand-up pouch, malleable box, or pliable bag. The package further includes a one-way degassing valve that is visible and accessible to a consumer (or other party) who may wish to pick up the container and squeeze it to experience the aroma(s) associated with the packaged bread crumbs (or other dry food product, e.g., spice, that may be packaged in the particular product). The valve may be any suitable degassing valve such as described previously. It may also be a degassing valve that does not include a filter or other element designed for or otherwise configured to retain aromatic compounds suspended in the air (or other gas(es)) in the container. The valve may be placed in any suitable location on the packaging, optimally, both visibly and physically accessible to the consumer. In some embodiments, the valve may be placed in the upper right-hand corner on the front of the packaging container, as shown in FIG. 1. Alternatively, the valve may be placed on any suitable surface of the packaging, such as on the top surface, any of the side surfaces, and may be placed at any location on this surface, such as on the side, corner, or in the middle.

In some embodiments, the packaged foodstuff (or other aromatic consumer product), e.g., breadcrumbs (medicinal marijuana products, etc.), may be dispensed into a four ounce stand-up pouch, such as a Plastic Bags for You, with an applied one-way degassing valve. The four ounce stand up pouch may be of any suitable size such as 5⅛"×8⅛"×3⅛". The packaging material may be made of any suitable material for preserving foodstuffs (and other consumer products) in the packaging, including linear low-density polyethylene, poly(ethylene terephthalate), aluminum, cardboard, or any other suitable packaging material. In some embodiments, the packaging may be heat-sealed, glued, taped, mechanically fixed, or sealed using any other suitable sealant. In some embodiments, the packaging may include a tear notch. In some embodiments, the seal may be formed above the tear notch.

Once foodstuffs (or other dry consumer products having an enticing and/or pleasant aroma when fresh) are dispensed into such suitable packaging, allowing for suitable air pressure for use and release of aroma(s), the package is then sealed such that the package, once sealed, contains sufficient gas or air so as to facilitate at least one, and preferably 2, 3, 4, 5, 6, 7, 8, 9, 10, or more consumer-initiated discharges of gas or air from the container's degassing valve before the packaged is opened and/or unsealed in order to access the foodstuff (or other product) packaged therein.

In some embodiments, provided herein are packaging containers and methods that may, on one hand, preferentially retain gases containing one or more aromatic compounds and, on the other hand, be induced to exhale those gases upon physical stimulation (e.g., by squeezing said container), such that the gas may be sampled by a consumer without compromising the integrity of the container or vessel and its ability to be serve as a non-chemical preservation method. The articles and methods described herein include, but are not limited to, the packaging and strategic marketing of dry consumer products (e.g., dry food products (e.g., breadcrumbs and breadcrumb-based products, spices, etc.), recreational and/or medicinal products that contain cannabis or marijuana (or extracts or derivatives thereof), potpourri (i.e., mixtures of dried plant products, for example, dried flower petals and/or spices), household cleaning products (e.g., soaps and other dry or powdered cleaning products)) having one or more appetizing flavors or aromas, are an appealing and salient product feature that can be exploited for enhanced marketing purposes. Surprisingly, however, such a feature has not previously been included in packaging for such products (e.g., foodstuffs, medicinal marijuana products, etc.).

Further provided herein are preservation devices for preserving dry consumer products (e.g., dry food products (e.g., breadcrumbs and breadcrumb-based products, spices, etc.), recreational and/or medicinal products that contain cannabis or marijuana (or extracts or derivatives thereof), potpourri (i.e., mixtures of dried plant products, for example, dried flower petals and/or spices), household cleaning products (e.g., soaps and other dry or powdered cleaning products)), etc. These devices include malleable packaging such as a bag, box, pouch, sleeve, container, and any other suitable packaging that allows consumer-initiated expulsion of air from the packaging, typically by way of a consumer applying a force to the exterior of the packaging, for example, by squeezing it in one or both hands so as to apply sufficient force to overcome the cracking pressure of the unidirectional outgassing valve disposed on the container. In such a device, the packaged consumer product (e.g., dry foodstuff) can preferably be preserved for a predetermined time (e.g., at least until the product's expiration date). As described herein, a preservation device of the invention may allow for aroma(s) to pass out of the device through the included valving structure, particularly when a consumer manually manipulates the packaging container in manner that increases the pressure inside the container above the cracking pressure of the unidirectional valve portion of the included valving structure.

Additionally provided herein are methods of using the devices of the invention. In some embodiments, these methods include sampling the aroma(s) of a dry consumer product (e.g., a dry food product (e.g., flavored or seasoned breadcrumbs or breadcrumb-based products, spices, etc.), recreational and/or medicinal products that contain cannabis or marijuana (or extracts or derivatives thereof), potpourri (i.e., mixtures of dried plant products, for example, dried flower petals and/or spices), household cleaning products (e.g., soaps and other dry or powdered cleaning products)), etc. packaged in container of the invention. Such methods generally involve including applying pressure to the container containing a desired dry consumer product whereby an aroma may pass through the valve so that a consumer may experience it. The user-directed releasing of the aroma(s) from inside of the container may include preventing the passage of solid components of the packaged foodstuff product while still allowing the passage of aromatic gases that provide the aroma(s) of the product.

Other methods include filling a container of the invention with a desired dry consumer product (e.g., dry food product (e.g., flavored or seasoned breadcrumbs and breadcrumb-based products, spices, etc.), recreational and/or medicinal products that contain cannabis or marijuana (or extracts or derivatives thereof), potpourri (i.e., mixtures of dried plant products, for example, dried flower petals and/or spices), household cleaning products (e.g., soaps and other dry or powdered cleaning products)), etc. Such methods typically include sealing the container after the dry consumer product (e.g., dry foodstuff product, medicinal marijuana products, etc.) has been added.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of sampling an aroma of a dry consumer product having an aroma that appeals to a consumer, the method comprising:
    applying pressure to a sealed container containing a dry consumer product having an aroma that appeals to a consumer, optionally a dry foodstuff product or cannabis-containing product, which container comprises (i) a malleable package that includes a unidirectional degassing valve disposed therein and (ii) prior to sealing, is at least partially inflated with gas to a pressure that is less than a cracking pressure of the unidirectional degassing valve, wherein after said inflation, when a consumer applies sufficient pressure to the sealed container so as to increase pressure inside the container above the unidirectional degassing valve's cracking pressure, gas is discharged from the container, thereby allowing the product's aroma to be sampled outside of, but without unsealing, the container.

2. The method of claim 1 wherein the unidirectional degassing valve comprises:
    a valve body;
    a one-way valve element positioned in the valve body; and
    a filter configured to prevent passage of solid components of the product but allow passage of aromatic compounds that contribute to the aroma of the product.

3. The method of claim 1 further comprising preventing the release of the product during sampling of its aroma.

4. The method of claim 1 wherein the container contains sufficient gas to facilitate 1, 2, 3, 4, 5, 6, 7, 8, 9, or 10 consumer-initiated discharges of gas from the container's unidirectional degassing valve before the container is unsealed.

5. The method of claim 1 wherein the gas is selected from the group consisting of air, carbon dioxide, oxygen, nitrogen, and methane.

6. The method of claim 1 wherein the product is cannabis.

7. A method of sampling an aroma of a dry consumer product comprising cannabis and having an aroma that appeals to a consumer, the method comprising:
    applying pressure to a sealed container containing a dry consumer product having an aroma that appeals to a consumer, which container comprises (i) a malleable package that includes a unidirectional degassing valve disposed therein and (ii) prior to sealing, is at least partially inflated with gas to a pressure that is less than a cracking pressure of the unidirectional degassing valve, wherein after said inflation, when a consumer applies sufficient pressure to the sealed container so as to increase pressure inside the container above the unidirectional degassing valve's cracking pressure, gas is discharged from the container, thereby allowing the product's aroma to be sampled outside of, but without unsealing, the container.

8. The method of claim 7 wherein the unidirectional degassing valve comprises:
    a valve body;
    a one-way valve element positioned in the valve body; and
    a filter configured to prevent passage of solid components of the product but allow passage of aromatic compounds that contribute to the aroma of the product.

9. The method of claim 7 further comprising preventing the release of the product during sampling of its aroma.

10. The method of claim 7 wherein the container contains sufficient gas to facilitate 1, 2, 3, 4, 5, 6, 7, 8, 9, or 10 consumer-initiated discharges of gas from the container's unidirectional degassing valve before the container is unsealed.

11. The method of claim 7 wherein the gas is selected from the group consisting of air, carbon dioxide, oxygen, nitrogen, and methane.

\* \* \* \* \*